United States Patent [19]

Reese et al.

[11] 4,279,885

[45] Jul. 21, 1981

[54] SOLID PHASE ASSAY

[75] Inventors: Max G. Reese, Salt Lake City; Dennis K. Ransom, Granger; LaVell R. Johnson, Salt Lake City, all of Utah

[73] Assignee: Becton Dickinson & Company, Paramus, N.J.

[21] Appl. No.: 907,741

[22] Filed: May 19, 1978

[51] Int. Cl.³ .................... G01N 33/48; G01T 1/00
[52] U.S. Cl. ............................ 424/1; 23/230 B; 424/12
[58] Field of Search ............. 424/1, 12; 23/230 B

[56] References Cited

U.S. PATENT DOCUMENTS 4,053,284  10/1977  Posch ........................... 424/1

OTHER PUBLICATIONS

Zettner et al. Clin. Chem., vol. 20, No. 1, 1974, pp. 5–14.

*Primary Examiner*—Benjamin R. Padgett
*Assistant Examiner*—Christine M. Nucker
*Attorney, Agent, or Firm*—Louis E. Marn; Elliot M. Olstein

[57] ABSTRACT

An analyte, such as an antigen, is initially contacted with a receptor (antibody) bound to a solid support, in the absence of tracer, followed by removal of unbound analyte and contacting with tracer. By separately contacting the receptor with analyte and tracer, sensitivity is increased.

8 Claims, No Drawings

SOLID PHASE ASSAY

This invention relates to the assay of ligands and more particularly to a new and improved solid phase competitive protein binding assay.

In a solid phase competitive protein binding assay, an antigen or hapten, for example, can be assayed by a method which involves competition between the analyte and a labeled form thereof for a limited number of receptor or binder sites bound to a solid support. Thus, for example, when a known quantity of a labeled form of the hapten or antigen, a known quantity of a receptor for the antigen or hapten, and a sample containing the hapten or antigen are combined and incubated, the percentage of the labeled form of the antigen or hapten bound to the receptor will vary inversely with the quantity of antigen or hapten in the sample. After separating the receptor bound antigen or hapten from the antigen or hapten not bound to the receptor or remaining in solution, the amount of labeled component in either or both fractions may be compared with a standard curve to determine the quantity of antigen or hapten which was present in the sample.

In accordance with the present invention, there is provided a solid phase competitive protein binding assay which has improved sensitivity.

In accordance with the present invention, the analyte is initially contacted with the receptor or binder bound to the solid support in the absence of tracer, followed by removal of unbound analyte and contacting with the tracer. It has been found that improved sensitivity can be obtained by not contacting the sample with the tracer; i.e., the sample is removed prior to the addition of tracer.

The analyte is most generally (1) an antigen which when introduced into the blood stream of a vertebrate, results in the formation of antibodies; (2) a hapten which when bound to an antigenic carrier and introduced into the blood stream of a vertebrate, produce antibodies specific for the hapten, or (3) ligands which have naturally occurring receptors and also function as a hapten when bound to a protein.

As representative examples of analytes to which the present invention is applicable, there may be mentioned: polypeptides, nucleotides, nucleosides and proteins, such as ACTH, oxytocin, leutenizing hormone, insulin, proinsulin, Bence-Jones protein, chorionic gonadotropin, pituitary gonadotropin, growth hormone, renin, thyroxine binding globulin, bradykinin, angiotensin, follicle stimulating hormone; cyclic AMP; cholyl glycine, cyclic GMP, etc.; steroids, including: estrogens, gestrogens, androgens, adrenocortical hormones, bile acids, cardiotonic glycosides, aglycones as well as saponins. As specific examples, these may be mentioned: thyroxine, triiodothyronine, testosterone, androsterone, equilenin, estrone, estriol, progesterone, pregnenolone, 17-hydroxydioxycorticosterone (compound S), deoxycorticosterone, cortisone, corticosterone, cortisol, aldosterone, digoxin, digitoxin, etc.; vitamins, such as vitamin A, folic acid, the B vitamin group, vitamin C, the D vitamins, and vitamins E and K; and miscellaneous ligands, such as antigens for Viral Hepatitis A and B, Rubella, Herpes Simplex, α-fetoprotein, carcinoembryonic antigen, etc.

The above substances are only representative, and it is understood that such substances can be used as appropriate analogs.

The tracer is the analyte or appropriate analog thereof having a "label" or "tag" which can be a radioisotope, an enzyme, a fluoroescent material, etc. The use of such labels or tags and the procedures for preparing a tracer containing such label or tag are well known in the art and no further details in this respect are needed for a complete understanding of the invention. The preferred tracer is radiolabeled, and as known in the art, such radioactive isotope is generally tritium or one of the radioisotopes of iodine.

The receptor or binder for the antigen or hapten can be an antibody or naturally occurring receptor.

The receptor is bound to support which is suitable as a substrate for an assay. As known in the art, such support materials include suitable polymers, such as polystyrene, polyethylene, polypropylene, polytetrafluoroethylene, polyamides, polyacrylamides, etc.; glass; bacterial cells; ion exchange resins; etc. Such solid supports are known in the art and no further details in this respect are deemed necessary for a full understanding of the invention. The receptor can be covalently or non-covalently bound to the support.

It is to be understood that in some cases the analyte is an antibody in which case the tracer is a labeled form of the antibody and the receptor is the corresponding antigen.

The present invention is particularly applicable to a solid phase assay in which the receptor or binder on a solid support is in a flow through chamber whereby the analyte is initially passed through the chamber containing the receptor on a solid support, followed by passing of the tracer through the chamber. It has been found that this procedure is an improvement over the prior procedure in which the analyte and tracer are mixed prior to passage through the chamber.

The present invention is most suited for an assay including regeneration of the receptor and the automation thereof, as described in U.S. Pat. Nos. 3,896,217 and 4,009,005.

In accordance with the automated procedure, the analyte is passed through a chamber containing a receptor for the ligand being assayed supported on a particulate support or substrate, in the absence of tracer, followed by passage of the tracer for the ligand through the chamber. The portion of the tracer which is passed through the chamber (unbound tracer) is collected and the amount of unbound tracer and/or bound tracer is determined. In accordance with such an automated assay, the tracer bound to the support is subsequently eluted therefrom by the use of a suitable elution solution thereby permitting reuse of the receptor.

The present invention is also applicable to assays which do not employ a flow through chamber; however, in such an assay the unbound analyte is generally removed by employing a washing step prior to addition of the tracer. The wash liquid may be any liquid which does not adversely affect the receptor, analyte and support and is generally one of the buffers used in the assay. It is to be understood that a washing step subsequent to addition of analyte and prior to addition of tracer may also be employed in an assay employing a flow through chamber.

In accordance with a preferred procedure, the tracer can be utilized in a buffer most suitable for the tracer and the analyte can be serum or other suitable preparation. In this manner, the amount of receptor in the chamber can be reduced, which increases sensitivity. Furthermore, the volume of analyte introduced into the chamber can be increased, which also increases the apparent sensitivity of the assay; i.e., it has been found that the sample volume can be increased in that tracer is not present in the sample and such increase in sample volume increases sensitivity.

The invention will be further described with respect to the following examples; however, the scope of the invention is not limited thereby:

EXAMPLE

The following materials are employed:

$^{125}$I-Thyroxine monolabeled with a specific activity of 250 mci/mg and diluted in sample buffer.

Thyroxine Antibody Chamber which is rabbit antiserum covalently attached to a solid support, and placed in a teflon chamber.

Adsorption Buffer is 0.1 M glycinate, pH 10.5, 0.01% bovine serum albumin, 5% ethyl alcohol, 300 ug/ml 8-anilino-1-naphthalene sulfonic acid, and 0.02% sodium azide.

In each case the sample volume is 0.5 ml, and in accordance with the invention the sample is initially passed through the chamber followed by passage of the tracer through the chamber. The percentage of tracer bound to the antibody is determined for each sample.

The procedure is repeated in accordance with the prior technique of premixing sample and tracer, prior to passage through the chamber.

The results are as follows:

| Thyroxine Concentration Ng/ml | Percent Invention | Binding Prior Art |
| --- | --- | --- |
| 1 | 43 | 49 |
| 2 | 35 | 48 |
| 4 | 28 | 40 |
| 7.5 | 19 | 33 |
| 15 | 15 | 25 |

The use of the procedure of the present invention results in a sensitivity which is about three times greater than the sensitivity which results from use of the prior art procedure.

The present invention is advantageous in that the assay sensitivity is increased. Moreover, non-specific binding to serum proteins is avoided.

These and other advantages should be apparent from the hereinabove description of the invention.

We claim:

1. In a competitive protein binding assay wherein an analyte and tracer are passed through a flow through chamber containing a receptor for both the tracer and analyte supported on a solid support, and at least one of the amount of tracer bound to the receptor and the amount of tracer which passes through the chamber is determined, the improvement comprising:

passing the analyte in the absence of tracer through said chamber to bind analyte to the receptor with any unbound analyte passing through the chamber; and subsequently passing tracer through the chamber to bind tracer to the receptor with any unbound tracer passing through the chamber.

2. The assay of claim 1 wherein a wash liquid is passed through the chamber subsequent to the passing of the analyte and prior to the passing of the tracer through the chamber.

3. The assay of claim 1 wherein the analyte contains an antigen.

4. The assay of claim 1 wherein the analyte contains a hapten.

5. The assay of claim 1 wherein the receptor is an antibody.

6. The assay of claim 1 wherein the assay is a radioassay and the tracer is radiolabeled.

7. The assay of claim 6 wherein the assay is an automated assay and bound tracer and bound analyte are subsequently eluted from the receptor.

8. The assay of claim 7 wherein the analyte contains thyroxine and the tracer is radioiodinated thyroxine.

* * * * *